United States Patent [19]

Holcomb

[11] 3,978,585

[45] Sept. 7, 1976

[54] IMPRESSION TRAYS

[76] Inventor: Burton V. Holcomb, 138 E. 13th St., Burley, Idaho 83318

[22] Filed: Apr. 5, 1974

[21] Appl. No.: 458,263

[52] U.S. Cl. .................................................... 32/17
[51] Int. Cl.² .......................................... A61C 9/00
[58] Field of Search ........................................ 32/17

[56] References Cited
UNITED STATES PATENTS

| 981,476 | 1/1911 | Rowse | 32/17 |
|---|---|---|---|
| 2,426,388 | 8/1947 | Chartrand | 32/17 |
| 2,452,866 | 11/1948 | Oertel | 32/17 |
| 2,802,269 | 8/1957 | Stern | 32/17 |

*Primary Examiner*—Robert Peshock

[57] ABSTRACT

The impression trays of this invention include an upper impression tray having a body which is a convoluted member having an oral plate which follows the general contours of the roof of the mouth and which provides a lingual portion adjacent the upper teeth, and buccal walls which are detachably mounted to the outer rectilinear edges of the body to form a depression in which impression compound may be disposed. This invention also includes a lower impression tray having a U-shaped body, including a trough-like portion corresponding to the base of the U-shape and to the incisors of the lower row of teeth, and a pair of mounting flanges issuing from the trough-like portion as legs of the U-shape, over the lower molar areas, and detachable buccal and lingual walls forming a trough-like depression into which the impression compound may be disposed.

5 Claims, 9 Drawing Figures

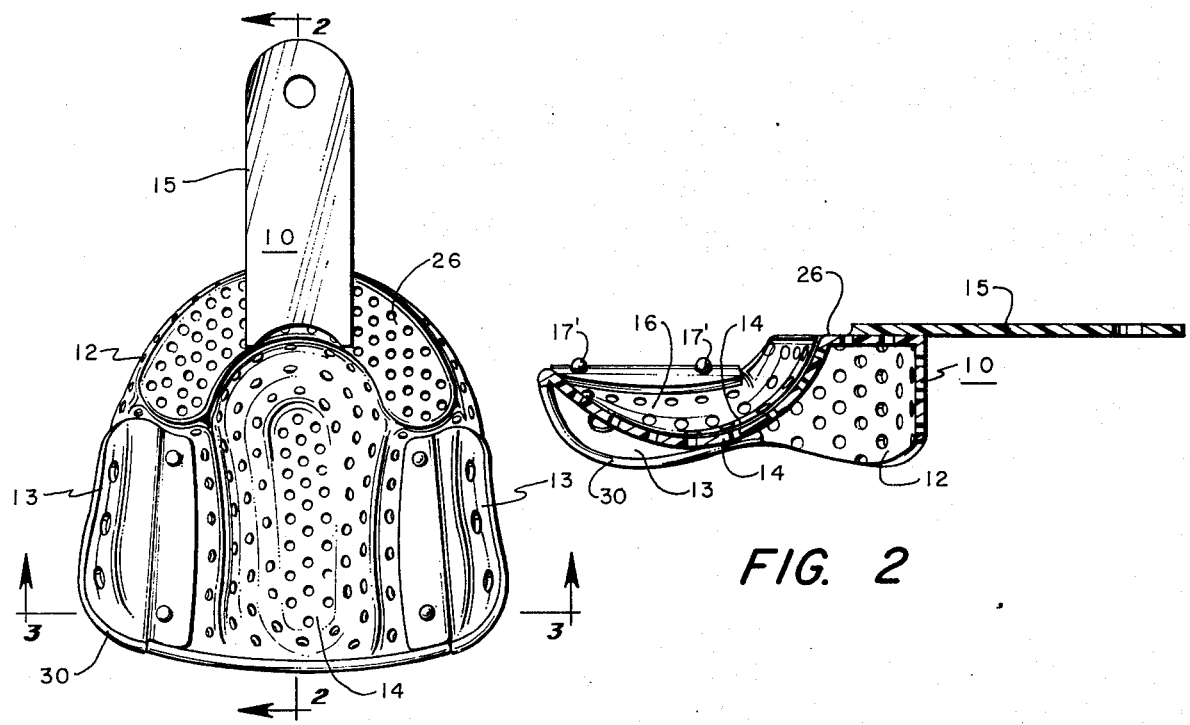
FIG. 1
FIG. 2
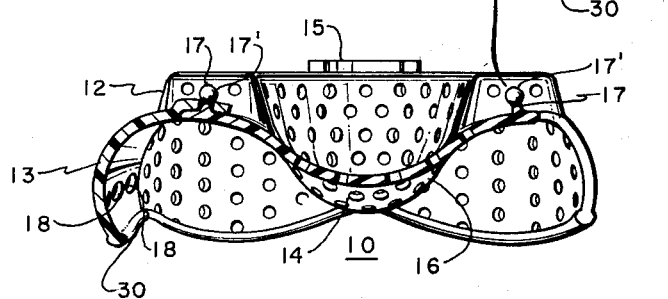
FIG. 3
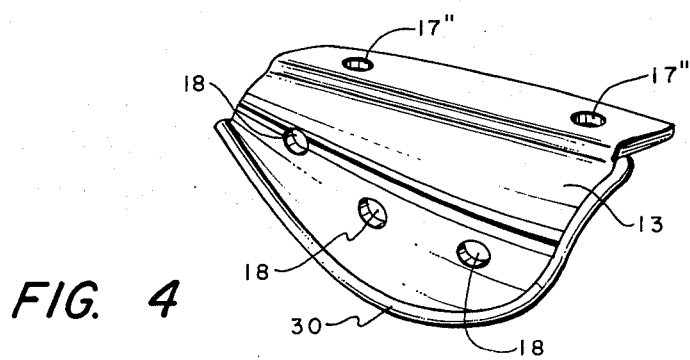
FIG. 4

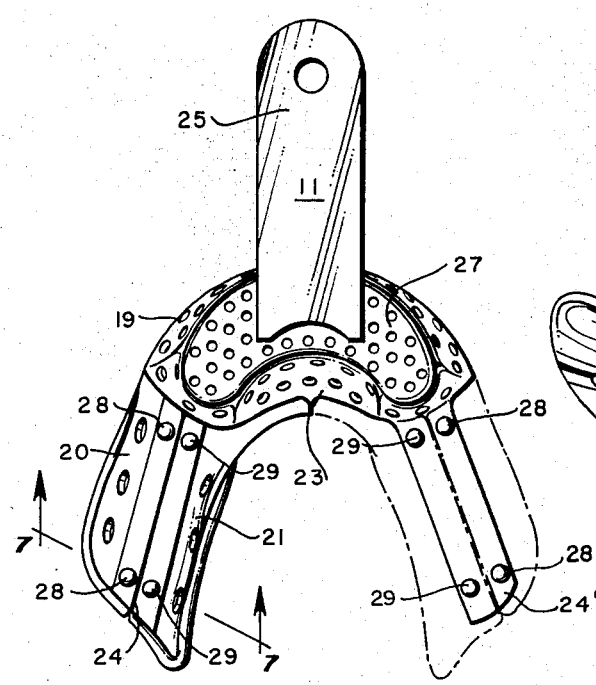
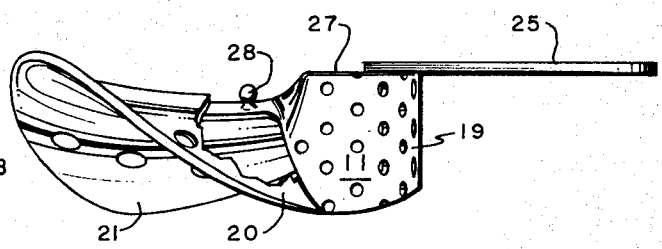
FIG. 5 FIG. 6
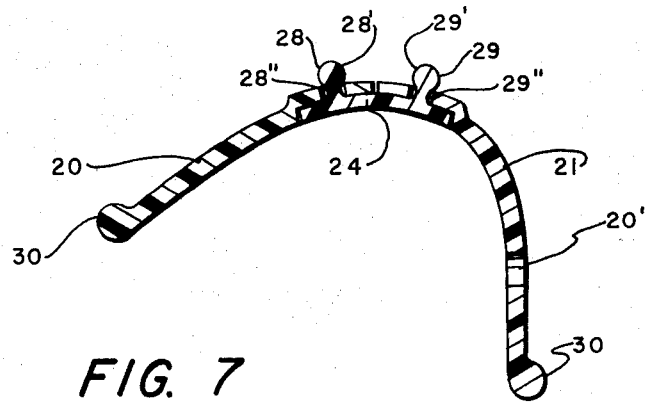
FIG. 7
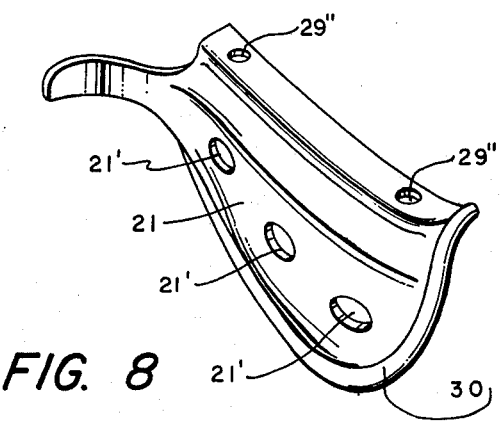
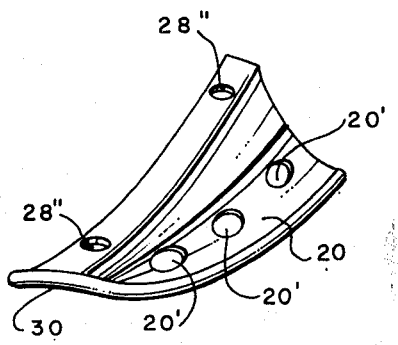
FIG. 8   FIG. 9

IMPRESSION TRAYS

FIELD OF INVENTION

The present invention relates to dentistry, and more particularly to trays for making impressions for dentures and the like.

DESCRIPTION OF THE PRIOR ART

Means heretofore used and employed for taking impressions for dentures, bridges, orthodontia, and the like, have included rigid, unitary trays having walls generally configured to follow contours of the respective upper and lower rows of teeth and gums. Thus, there is typically provided a tray for holding impression compound for the upper teeth which may include a portion conforming to the roof of the mouth; and a tray for the lower row of teeth. The respective trays may be for a full or partial row of teeth. Trays are typically fabricated to fit several predetermined classes of mouth size. Seldom does the individual patient have the proportions of the tray. This is particularly true for the depth of the outside or buccal wall and the lingual wall.

Accordingly, it is an object of the present invention to provide a tray for taking dental impressions having detachable walls adjacent teeth and gums which may be selected to permit proper fitting for each patient.

It is also an object of this invention that the lower impression tray have both detachable buccal and lingual wall members.

It is a further object that means securing the detachable walls to the tray body be structurally simple and be operable to rigidly lock the respective members.

These and other objects shall become apparent from the description following, it being understood that modifications may be made without affecting the teachings of the invention here set out.

SUMMARY OF THE INVENTION

The impression trays of this invention include an upper impression tray having a body which is a convoluted member having an oral plate which follows the general contours of the roof of the mouth and which provides a lingual portion adjacent the upper teeth, and buccal walls which are detachably mounted to the outer rectilinear edges of the body to form a depression in which impression compound may be disposed. This invention also includes a lower impression tray having U-shaped body including a trough-like portion corresponding to the base of the U-shape and to the incisors of the lower row of teeth, and a pair of mounting flanges issuing from the trough-like portion as legs of the U-shape, over the lower molar areas, and detachable buccal and lingual walls forming a trough-like depression into which the impression compound may be disposed.

A more thorough and comprehensive understanding may be had from the detailed description of the preferred embodiment when read in connection with the drawings forming a part of this specification.

BRIEF DESCRIPTION OF THE DRAWINGS

FIG. 1 is a bottom plan view of an upper impression tray of this invention.

FIG. 2 is a cross-sectional view taken substantially along the lines 2—2 of the FIG. 1.

FIG. 3 is cross-sectional view taken substantially along the lines 3—3 of the FIG. 1 with a portion of the buccal walls exploded away for illustrative purposes.

FIG. 4 is a perspective view of a typical right buccal wall of this invention.

FIG. 5 is a top plan view of a lower impression tray of this invention.

FIG. 6 is a fragmentary side elevational view of the apparatus of FIG. 5 shown with a portion of the buccal wall broken away for illustrative purposes.

FIG. 7 is a cross-sectional view taken substantially along the lines 7—7 of the FIG. 5.

FIG. 8 is a perspective view of a typical lingual wall of the lower impression tray.

FIG. 9 is a perspective view of a typical buccal wall of the lower impression tray.

DETAILED DESCRIPTION OF THE PREFERRED EMBODIMENT

Referring now to the drawings and more particularly to the FIGS. 1 and 5, the upper and lower impression trays of this invention are shown to advantage and generally identified by the numerals 10 and 11, respectively. The upper impression tray 10 may be used in combination with, or separate from, the lower impression tray 11 in making impressions for dentures and dental appliances. It is to be understood that, although full impression trays 10 and 11 are described herein, partial trays may designed employed the teachings of this invention.

As shown in the FIGS. 1, 2, and 3, the upper impression tray 10 comprises a body 12 and an outer or buccal wall 13 along each of the rectilinear sides of the body 12. The body 12 is a rigid structure which may be fabricated of metal or rigid polymer comprising an oral plate 14 and a handle 15. The oral plate 14 is a convoluted member which follows the contours of roof of the mouth. The oral plate 14 and body 12 may be fabricated with a multiplicity of holes which may be perforated to permit nominal tying of impression compound. The portions of the oral plate 14 adjacent the teeth are convoluted to form a lingual or inside wall 16. As shown in the FIGS. 3 and 4, the buccal or outside wall 13 is a convoluted member having a right-angle curved vertical cross-section, wherein the upper horizontal portion includes means for detachably securing the buccal 13 to the outer, sidewardmost terminal edge of the oral plate 14. Means for securing the buccal 13 and the body 12 should be operable to suitably rigidly lock the members with little tolerance. Means for securing may include commonly known snap locks 17 having a projecting knob or bead 17' and a complementary hole 17'' on the buccal 13 of the body 12, respectively. Other means may include tongues and grooves, and the like. The buccal 13 may include a plurality of perforations 18 in the manner of perforations set out above with respect to the oral plate 14 which are operable to provide means for retaining impression compound as will be hereinafter described. It may be seen that the detachable buccal wall 13 and the lingual portion 16 of the oral plate 14 form a trough-like depression into which impression compound may be disposed.

It is to be understood that a set of buccals 13 of varying sizes may be provided for a single predetermined size of the body 12. The buccals 13 of varying sizes may differ in width, curvature, or impressions and contours. These elements may be seen in a typical detachable buccal 13 shown in the FIG. 4.

The handle 15 issues forwardly from the lowermost terminal side of the body 12, or from the side opposite the side carrying the impression compound. As shown in the FIG. 2, the handle 15 may be fastened to the plate 14 to provide means for aligning a similar, flat side on the lower impression tray 11, as shall become apparent.

Referring now to the FIGS. 5, 6, and 7, the lower impression tray 11 comprises a body 19, a buccal or outside wall 20, and a lingual or inside wall 21. The body 19 is a substantially U-shaped member having a trough-like portion 23 corresponding to the base of the U-shape and to the incisors of the lower row of teeth of the mandibular jaw, and a pair of mounting flanges 24 and 24' issuing from the trough-like portion 23 as distally extended legs of the U-shape, over the lower molar areas. Like the body 12, the portion 23 may be perforated to permit nominal tying of the impression compound. A handle 25, like the handle 15, issues forwardly from the center of the trough-like portion 23. As shown in the FIGS. 2 and 6, the lowermost side of the forward portion of the upper impression tray 10 and the uppermost terminal side of the lower impression tray 11 may be provided with a flat side 26 and 27, respectively, which may be used as a convenient resting point for distribution of impression compound. This flat portion may also be of some use in lining or inserting the trays into the mouth.

The mounting flanges 24 and 24' are intended to detachably carry the buccal 20 and the lingual 21. As shown in the FIG. 7, the flanges 24 and 24' may be secured by any of a number of detachable securing means operable to rigidly lock the members with a small tolerance. Means securing may include snap locks 28 and 29 having a projecting knob or bead 28' and 29', and complementary holes 28'' and 29'' in the respective buccal 20 and lingual 21 to the body 19. The buccal 20, like the buccal 13, is a convoluted member having a vertical cross-section having a predetermined curvature convex to the interior center of the lower tray 11. As above, it is intended that a set of buccals 20 be provided for a body 19 having a predetermined rectilinear width, curvature, or impressions and contours. These elements may be seen in a typical detachable lower impression tray buccal 20 as shown in the FIG. 9. The buccal 20 may also include perforations 20' which facilitate retaining of impression compound in the lower tray 11.

Similarly, as shown in FIG. 8, the lingual 21 is convoluted member convex to the interior center of the tray 11, which together with the buccal 20 forms a trough-like region operable to hold a predetermined amount of impression compound. As above, it is intended that a plurality of linguals 21 be provided for a body 19 to vary with demands of rectilinear width, curvature, or impressions and contours. As above, the lingual 21 may be provided with perforations 21' to facilitate retaining of impression compound. It may be seen that the linguals 21 may be fabricated with a detachable buccal 20. It is to be understood that a set of linguals 21 and buccals 20 of selected sizes may be provided for a single predetermined size of the body 19 as set out above with respect to the body 12.

It has been found to advantage that fabricating the bodies 12 and 19 and their respective flanges of a suitable rigid polymer may provide means for conforming by hand the individual trays 10 and 11 to better coincide with their respective jaws and the contour of the rows of teeth.

It may also be seen that providing a beaded or rolled terminal edge around the uppermost and lowermost terminal edges of the respective trays 10 and 11 and their respective buccal and lingual, flanges as shown in the FIG. 4 and generally designated 30, faciliates the retaining of impression compound in addition to providing reinforcement.

In operation, a body 12 and a body 19 may be selected for jaw width for the respective upper tray 10 and lower tray 11, respectively. The upper tray 10 may then be prepared by engaging suitable buccal wall 13 to the body 12 which generally fit the particular dimensions of the patient. Similarly, the lower tray 11 may be prepared by engaging both suitable buccals 20 and linguals 21 to the mounting flange portions 24 and 24'. The trays may then be filled with impression compound in the manner commonly followed.

Having thus described in detail a preferred apparatus which embodies the concepts an principles of the invention and which accomplishes the various objects, purposes and aims thereof, it is to be appreciated and will be apparent to those skilled in the art that many physical changes could be made in the apparatus without altering the inventive concepts and principles embodied therein. Hence, it is intended that the scope of the invention be limited only to the extent indicated in the appended claims.

I claim:

1. An upper impression tray comprising a body which is a convoluted member having an oral plate which follows the general contours of the roof of the mouth and which provides a lingual portion adjacent the upper teeth, and buccal walls which are detachably mounted by snap lock elements to the outer rectilinear edges of the body, to form a depression in which impression compound may be disposed.

2. A lower impression tray having a U-shaped body, a trough-like portion corresponding to the base of the U-shape and to the incisors of the lower row of teeth, and a pair of mounting flanges issuing from said trough-like portion as legs of the U-shape, over the lower molar areas, and a lingual walls being detachably mounted to and issuing interiorly from said mounting flanges; and a buccal wall detachably mounted to said body forming a trough-like depression into which impression compound may be disposed.

3. The apparatus of claim 2 wherein said lingual wall is detachably mounted to said mounting flanges.

4. The apparatus of claim 2 wherein said buccal walls are detachably mounted to said mounting flanges by snap locks.

5. The apparatus of claim 3 wherein said lingual walls are detachably mounted to mounting flanges by snap locks.

* * * * *